United States Patent [19]

Glonek et al.

[11] Patent Number: 5,294,607

[45] Date of Patent: * Mar. 15, 1994

[54] DRY EYE TREATMENT PROCESS AND SOLUTION

[75] Inventors: Thomas Glonek, Oak Park, Ill.; Jack V. Greiner, Winchester; Donald R. Korb, Boston, both of Mass.

[73] Assignee: Ocular Research of Boston, Inc., Boston, Mass.

[*] Notice: The portion of the term of this patent subsequent to Jan. 11, 2011 has been disclaimed.

[21] Appl. No.: 898,375

[22] Filed: Jun. 9, 1992

Related U.S. Application Data

[63] Continuation of Ser. No. 638,215, Jan. 7, 1991, abandoned, which is a continuation-in-part of Ser. No. 529,657, May 29, 1990, abandoned.

[51] Int. Cl.$^5$ .................. A61K 31/685; A61K 31/66; A61K 31/20
[52] U.S. Cl. ......................... 514/76; 514/75; 514/78; 514/558; 514/912
[58] Field of Search .................. 514/75, 76, 78, 558, 514/912

[56] References Cited

U.S. PATENT DOCUMENTS

| | | | |
|---|---|---|---|
| 4,421,748 | 12/1983 | Trager et al. | 424/199 |
| 4,677,099 | 6/1987 | Shinitzky et al. | 514/78 |
| 4,804,539 | 2/1989 | Guo et al. | 424/450 |
| 4,818,537 | 4/1989 | Guo | 424/427 |
| 4,839,175 | 6/1989 | Guo | 424/450 |
| 4,866,049 | 9/1989 | Maumenee et al. | 514/169 |
| 4,914,088 | 4/1990 | Glonek | 514/76 |

FOREIGN PATENT DOCUMENTS

| | | |
|---|---|---|
| 16149 | 1/1978 | Australia . |
| 0391369 | 4/1990 | European Pat. Off. . |

OTHER PUBLICATIONS

Hardberger, Hanna and Boyd, "Effects of Drug Vehicles on Ocular Contact Time," *Arch Ophthalmol*, vol. 93, Jan. 1975.

F. Holly, *Contacto*, 26(5), pp. 9-13 (Sep., 1982).

Federal Register, 7076-7093 (Mar. 4, 1988).

*Primary Examiner*—Zohreh A. Fay
*Attorney, Agent, or Firm*—Robert L. Goldberg

[57] ABSTRACT

A method and composition for reducing evaporation of an aqueous layer from the surface of the eye. The method comprises applying an admixture of a charged phospholipid and a non-polar oil over the eye, preferably in the form of a meta-stable oil in water emulsion in a dosage not exceeding 100 microliters.

46 Claims, No Drawings

DRY EYE TREATMENT PROCESS AND SOLUTION

CROSS REFERENCE TO RELATED APPLICATIONS

This is a continuation of Ser. No. 07/638,215, filed Jan. 7, 1991, now abandoned, which is a continuation, in part, of copending U.S. patent application Ser. No. 07/529,657, filed May 29, 1990, now abandoned.

BACKGROUND OF THE INVENTION

1. Introduction

This invention relates to wetting the surface of the eye and/or an ocular prosthesis, providing mechanical lubrication therefor, reducing the evaporation of fluid from the surface of the eye and if desired, delivering a medicament to the ocular surface. More particularly, the invention relates to a composition capable of augmenting and maintaining a stable tear film over the ocular surface and/or delivering a medicament to said surface without causing substantial blurring of vision. In a preferred embodiment of the invention, the invention relates to an ophthalmic composition for dry eye treatment. The invention is especially useful for treatment of individuals wearing ocular prostheses such as contact lenses, as the composition of the invention wets and provides lubrication for both the ocular surface and the surface of the prosthesis in contact with the ocular surfaces.

2. Description of the Prior Art

It is known in the art that an aqueous tear film extend over the ocular surfaces and maintains the ocular surface moist and lubricated. It is also known that dehydration of moisture from the eye may result in discomfort. Further, it is known that compositions are available in the market intended for dry eye treatment. These compositions are primarily aqueous materials that supplement the tear film.

The feeling of discomfort resulting form a dry eye condition may include ocular dryness, grittiness, burning, soreness or scratching, dependent upon the subject and the condition of the subject. Proposed causes for dry eye, treatment and symptoms are described in a compendium of papers edited by Holly, *The Preocular Tear Film in Health, Disease, and Contact Lens Wear*, The Dry Eye Institute, Lubbock, Tex. 1986, incorporated herein by reference.

The most common treatment for dry eye involves temporary alleviation of dry eye symptoms by topical application of a tear substitute that adds a large volume of liquid to the anterior surface of the eye and related adnexa. Typical tear substitute compositions comprise water soluble polymer solutions. Examples of such solutions include saline solutions of polyvinyl alcohol, hydroxypropylmethyl cellulose or carboxymethyl celluloses. U.S. Pat. No. 4,421,748 teaches an artificial tear composition comprising an aqueous hypotonic solution of lecithin and a viscosity adjusting agent such as a solution soluble cellulose.

Methods used to quantify the effectiveness of tear substitutes for dry eye treatment solutions have not been standardized, and many methods used to quantify the results obtained using such tear substitute compositions are often inaccurate. For this reason, it is known that reported relief of dry eye symptoms using known tear substitutes varies considerably from subject to subject, and regardless of the method used to quantify relief using a tear substitute, relief often does not exceed several minutes.

The symptoms associated with dry eye are often exacerbated with subjects using ocular prostheses such as contact lenses. In some cases, contact lens intolerance is caused in part, or in total, by the condition of dry eye and its symptoms. Further, the rate of evaporation from the eye is accelerated by the nature of the contact lens surface and the physical presence of the contact lens results in meniscii formation with additional physical and evaporative effects, even with subjects having an adequate tear film. For many subjects, contact lens intolerance is not overcome by topical application of tear substitutes. Therefore, there is a need for improved compositions and processes for treatment of the dry eye condition and for improving tolerance to ocular prostheses.

An improved composition for dry eye treatment is the subject of U.S. Pat. No. 4,914,088 incorporated herein by reference. This patent teaches the use of charged phospholipids for the treatment of dry eye symptoms. The addition of a charged phospholipid to the eye assists in replicating the tear film that would naturally occur in the eye. In accordance with the patent, the phospholipid composition, preferably in the form of an aqueous emulsion, is topically applied to the eye where it is believed to disperse over the ocular surface and form a film that replicates a lipid layer that would be formed by the spreading of a naturally occurring lipid secreted principally from the Meibomian glands during blinking. Because the phospholipid, when applied to the eye, carries a net charge, it is believed that aligned molecules repel each other preventing complex aggregate formation thereby resulting in a stable phospholipid film. The patent speculates that the film formed from the charged phospholipid assists in the formation of a barrier film reducing evaporation of the aqueous layer, thereby preserving the tear film.

In copending U.S. patent application Ser. No. 07/529,657, filed May 29, 1990, a further improvement in dry eye treatment is disclosed. In accordance with the disclosure of said application, the dry eye treatment composition of U.S. Pat. No. 4,914,088 is improved by the addition of an essentially non-polar oil to the eye treatment composition. The oil is added to improve the performance of a dry eye treatment composition by increasing the longevity of the tear film formed on the eye following addition of the dry eye treatment solution, presumably by providing and/or thickening the dehydration barrier (the oil layer) on the outer surface of the tear film. Thus, the oil increases the efficacy of the dry eye treatment solution and reduces performance variability from subject to subject.

The use of the dry eye treatment of the referenced application assists in overcoming dry eye symptoms as reported in the application. However, when using the procedures and composition of the application, some subjects experience blurring following addition of the treatment composition containing the oil. The time required for the blur to clear is often unpredictable. In addition, relief of dry eye symptoms was found to vary somewhat from patient to patient.

SUMMARY OF THE INVENTION

The invention disclosed herein is a further improvement over the inventions disclosed in the above referenced U.S. Pat. No. 4,914,088 and copending application Ser. No. 07/529,657. In accordance with the invention disclosed herein, dry eye treatment compositions and processes are further improved by providing a controlled means for application of a dry eye treatment composition to the eye whereby blurred vision is reduced or eliminated and the residence time of tear film on the eye is prolonged.

The invention herein is the result of several discoveries. First, it has been discovered that the total quantity of oil available to form a film over the ocular surface should be closely controlled. Secondly, and contrary to prior understanding, it has been found that when the dry eye treatment composition is in the form of an emulsion, the emulsion is preferably added to the eye as a meta-stable emulsion, not as a finely divided, stable emulsion. Finally, it has been discovered that the surfactant used in the preparations of the preferred treatment composition be one that enables control of the amount of oil contained in an emulsion and enables rapid formation of an oil film over the ocular surface.

To understand how the treatment compositions of the invention function and the basis for the improvements described herein, it is desirable to understand the mechanism by which a barrier film over the eye is capable of alleviating dry eye symptoms. The description that follows is based upon belief and that reported in the literature.

It is reported that a naturally occurring tear film comprises a complex coating with three separate layers. The inner layer in contact with the ocular surface of the eye is said to be composed primarily of mucous, and renders the hydrophobic epithelial cell surface hydrophilic. The middle layer of the tear film is an aqueous layer. This layer is the thickest portion of the tear film, is a source of moisture and lubrication for the eye and functions as an optical planarizing layer. The outer layer of the tear film, at the interface with the atmosphere, is a non-polar oily, naturally occurring lipid layer. This oily lipid layer is reported to act as a barrier that prevents evaporation of the aqueous layer (Mishima and Maurice: The oily layer of the tear film and evaporation from the corneal surface, Exp. Eye Res. 1961; 1:39–45). Finally, the oily layer is bound to the aqueous layer through a polar interfacial phospholipid layer.

The polar phospholipid and non-polar oily lipid components of the tear film are thought to originate primarily from secretions of the Meibomian glands. The oily layer of the tear film is formed from these secretions and is constantly replenished during blinking by expression of the secretions from the Meibomian glands and then spreading of the same over the surface of the eye by the eyelids. By constantly spreading the polar and non-polar lipids over the eye during blinking, the tear film is maintained and evaporation of the aqueous middle layer of the tear film is minimized.

A cause of dry eye is believed to be a deficiency in the quantity or quality of secretions from the Meibomian glands. It is postulated herein that a cause of dry eye is a deficiency in the polar lipid layer of the tear film, the non-polar oily lipid layer or both. Regardless of the cause of the deficiency, the compromised lipid layer fails to act as an adequate barrier against evaporation of the aqueous portion of the tear film resulting in one form of the dry eye condition.

In accordance with the invention of U.S. Pat. No. 4,914,088, a charged phospholipid is added to the eye, preferably as an oil-in-water emulsion. Upon contact of the emulsion with the eye, it was thought that the phospholipid dispersed over the ocular surface to form a film replicating the lipid layer formed by spreading a naturally occurring lipid secreted from the Meibomian glands during blinking. Where the phospholipid applied to the eye preferably carries a net charge, it is believed that the aligned molecules repel each other such that complex aggregate formation is prevented and the integrity of the phospholipid film is maintained. It was believed that the film formed from the phospholipid layer acted as a barrier, reducing evaporation of the aqueous layer, thereby preserving the tear film.

In practice, it was found that treatment of dry eye symptoms with the phospholipid compositions claimed in U.S. Pat. No. 4,914,088 resulted in substantial improvement relative to treatment with prior art compositions. Films formed by the application of the phospholipid to the eye were found to be long lasting and application of the treatment composition did not cause blurring of vision any more severe than the blurring resulting from the application of prior art compositions for dry eye treatment or even physiological saline.

Though the use of the dry eye treatment compositions of U.S. Pat. No. 4,914,088 provided relief of dry eye symptoms in the majority of patients treated as stated in said patent, with improved testing procedures developed subsequent to the filing of the application leading to the grant of said patent, it was found that there was variance in efficacy from patient to patient.

In copending U.S. patent application Ser. No. 07/529,657, an improved dry eye treatment composition is disclosed. The invention of the application was the discovery of the desirability of adding an oil to the eye for treatment of the dry eye condition. Thus, the invention of the copending application involved supplementing dry eye treatment by addition of an essentially non-polar oil to the eye. In a preferred embodiment of the invention, dry eye treatment involved adding a combination of a charged phospholipid and an essentially non-polar oil to the eye. In accordance with said application, though the charged phospholipid and the non-polar oil could be separately applied to the eye, it was preferred that the two components be combined in a single treatment composition, most preferably in the form of a finely divided stable oil-in-water emulsion. A stable emulsion was desired for long term storage in a container. Upon application of the phospholipid and oil to the eye, whether as separate additions or as a single treatment composition, it was postulated that the negatively charged phospholipid layer formed an aligned film over the aqueous tear film with charged ends dissolved in the aqueous layer and hydrophobic ends furthest removed from the aqueous layer available to bond with the non-polar oil layer. This caused the oil layer to disperse over the top surface of the eye as a thin, continuous and stable layer that functioned as an evaporation barrier. Recognizing that the tear film naturally occurring in the eye may be deficient in the phospholipid component, the oil component, or both, the preferred embodiment of the treatment composition of said application replenished both components of the tear film, thereby reducing variations in efficacy from patient to patient.

Use of the treatment compositions of the copending application results in formation of a tear film over the eye that alleviates dry eye symptoms and increases patient tolerance for ocular prostheses as described in said application. However, as a consequence of treatment with the solution, some subjects experienced blurred vision both initially upon application of the treatment composition to the eye, and in some cases over a prolonged time. In accordance with the invention described herein, the dry eye compositions alleviate dry eye symptoms at least as effectively as those of the above-referenced copending application, enhance patient tolerance to ocular prostheses, and provide the further advantage of essentially avoiding prolonged blurred vision. In addition, in accordance with the subject invention, the residence time of the film is increased.

In accordance with the invention, it has been found that the above described improvements are realized if any one or more of the following is practiced:

(1) the total amount of oil comprising the film over the ocular surface is controlled;

(2) the treatment composition is added to the eye in the form of a meta-stable emulsion; and (3) the treatment composition, in the form of an emulsion, contains a surfactant that permits increase in the oil content of an emulsion with decreased phospholipid content and enables rapid formation of a film of the efficacious components of the treatment composition over the ocular surface.

With regard to control of the amount of oil comprising the film over the eye, it should be recognized that the oil layer is a thin film and the total volume of oil required to form this thin film is extremely small. If the oil component of the tear film is excessively thick or irregular (beaded), the patient will experience prolonged blurred vision. The problem is exacerabated when the oil is a polar oil rather than the preferred non-polar oil.

The process of formation of a tear film following addition of a treatment composition to the eye is a dynamic process with many steps involved. If the treatment composition is in the form of an emulsion, several processes are simultaneously set in motion immediately following the addition of the emulsion to the eye. The emulsion begins to differentiate while the dispersed oil phase spreads over the ocular surface. In addition, the amount of a fluid additive retained by the eye is up to about 10 microliters (ul). It is believed that if the volume of a fluid additive increases above about lo ul, excess fluid moves to the canthi and rapidly enters the tear duct or is expressed from the eye as tears. This can occur within four to five blinks following addition of the treatment composition to the eye. Discharge of excess fluid will result in discharge of treatment components of the fluid from the eye, making them unavailable to form and sustain the tear film. This problem is exacerbated if the fluid is in the form of an emulsion which does not rapidly differentiate liberating treatment components. Consequently, the concentration of the treatment components of the emulsion must be sufficient to treat the eye and compensate for that lost by discharge from the eye but should not be excessive and cause blurring.

In accordance with the invention, recognizing that the formation of a tear film is a dynamic process as described above, the total amount of oil available for formation of a film preferably does not exceed 25 ul, more preferably varies between about 1 and 10 ul and most preferably varies between about 1 and 5 ul. Of this amount, only a small portion will be available to form the oil layer over the ocular surface. As the amount of oil available for film formation exceeds about 10 ul, the oil film formed over the eye becomes excessively thick or, alternatively, oil globules may form on the surface of the eye and not spread evenly over the eye. In either case, the patient is likely to experience blurring due to excessive oil. The amount of oil beyond which blurring will occur varies from patient to patient and is dependent upon the specific oil uses.

The treatment compositions of the invention are desirably formulated to permit self administration by a patient. It is difficult for a patient to self-administer low volumes of treatment composition—i.e., amounts of from 1 to 10 ul. Therefore, to render the formulations suitable for self-administration, it is desirable to disperse the active compounds of the formulation in a suitable vehicle that permits administration of larger volumes by the patient. To control the volume of oils available for formation of the tear film without excessive discharge of treatment composition from the eye and to provide water to augment the aqueous portion of the tear film, the total amount of a liquid treatment composition added to the eye per treatment per eye preferably does not exceed 100 microliters (ul) (about 2 drops) and more preferably varies between about 25 and 50 ul. Since it is desired to limit the total volume of treatment composition added to the eye while recognizing that excess is discharged from the eye by blinking, and that the total volume of oil must be controlled, it is apparent that the concentration of oil in the treatment solution must be adjusted to provide the desired small dosage of oil to the eye and compensate for that lost due to discharge of excess treatment composition.

For reasons stated above, rapid formation of the oil film over the corneal surface is desirable. If the film does not form rapidly, oil in the treatment composition may be discharged from the eye before it can form a satisfactory film. When oil is added in the form of an emulsion, the emulsion should differentiate rapidly on entering the eye to provide oil for formation of a film before excessive oil is discharged from the eye with excess treatment composition. The formation of the oil film is desirably assisted by use of a surfactant in the treatment composition which assists in spreading the oil over the eye. The surfactant should be one that enables rapid phase differentiation and further, should be one compatible with composition components and physiologically compatible with the eye—i.e., it should not be toxic nor cause stinging.

From the above discussion, it is apparent that it is undesirable to provide a treatment composition in the form of an excessively stable emulsion for several reasons. An emulsion is often optically opaque due to the presence of distinct dispersed phases. Therefore, an emulsion over the surface of the eye is expected to cause blurring. The duration of blur is dependent upon the time required for the emulsion to differentiate and form separate layers replicating a tear film. Consequently, blurring is likely to occur until the emulsion differentiates. In addition, and as discussed above, if the emulsion is too stable, excess emulsion will be discharged from the eye. Discharge of the emulsion from the eye will result in discharge of efficacious components of the treatment solution from the eye before a tear film can be formed and these components will not be available for formation of the tear film. Therefore, in accordance with this invention, it is preferred that the emulsion be stable for long term storage, but rapidly differentiate in the eye. This is difficult to achieve with existing technology and for purposes herein it is desired that the emulsion be meta-stable where a meta-stable emulsion is defined as a composition that is sufficiently stable to provide a uniform dose to the eye but is relatively unstable and rapidly differentiates upon contact with the eye, preferably differentiating within about 5 blinks following application of the composition to the eye, more preferably in a time of less than about 30 seconds. Blurring may occur during the time required to move the bulk of the excess liquid to the canthi and discharge the same from the eye.

In accordance with the copending application, non-polar oils were used for dry eye treatment because the use of polar oils caused substantial blurring. It is a further discovery of this invention that though non-polar oils are preferred, polar oils may be used to alleviate dry eye symptoms without significant blurring if their volume available for film formation is carefully controlled within the most preferred concentration range of from 1 to 5 ul, more preferably 1 to 3 ul or if the polar oils are diluted with non-polar oils.

Based upon the above, the invention described herein comprises treatment of the eye with either a charged phospholipid, an oil, preferably an essentially non-polar oil, or both, in amounts and in a treatment solution form that reduces or eliminates blurring and prolongs the residence time of an artificially formed replicated tear film on the eye.

DESCRIPTION OF THE PREFERRED EMBODIMENTS

The treatment compositions of the invention comprise an oil, a charged phospholipid or bath. They are applied by topical application to the eye. Topical application is by application of each component separately or preferably by single treatment composition containing the two components in a single liquid vehicle such as an emulsion. More preferably, the emulsion is an aqueous oil-in-water, meta-stable emulsion where the oil comprises the dispersed (organic) phase of the emulsion.

Phospholipids suitable for purposes of the invention are known in the art to be complex and to carry a net positive or negative charge under conditions of use. The preferred materials are those carrying a net negative charge because the negatively charged material will be repelled by the negatively charged ocular surface thereby permitting the maintenance of a relatively thick aqueous layer. The positively charged phospholipid will be attracted to the negatively charged ocular surface thus compressing the tear film. Hence the positively charged phospholipids operate in a different manner than the negatively charged phospholipids and are lesser preferred.

It is known that complex phospholipids contain a polar group at one end of their molecular structure and a non-polar group at the opposite end of the molecular structure. A discussion of phospholipids can be found in Leninger, *Biochemistry*, 2 ed., Worth Publishers, N.Y., pp. 279-306, incorporated herein by reference. Many complex phospholipids are known in the art. They differ in size, shape and the electric charge of their polar head groups. Phosphoglycerides are compounds where one primary hydroxyl group of glycerol is esterified to phosphoric acid, and the other two hydroxyl groups are esterified with fatty acids. The parent compound of the series is, therefore, the phosphoric acid ester of glycerol. This compound has an asymmetric carbon atom and, therefore, the term phosphoglycerides includes stereoisomers.

All phosphoglycerides have a negative charge at the phosphate group at pH 7, and the $pK_a$ of this group is in the range of 1 to 2. The head groups of phosphatidylinositol, phosphatidylglycerol including diphosphatidylglycerols (having the common name cardiolipins) and the phosphatidylsugars have no electric charge, and all are polar because of their high hydroxyl group content. Because of the negative charge of the phosphate group and the absence of a charge in the head group, the net charge of each of these materials is negative, and these materials are within the scope of the invention. Likewise, the head group of phosphatidylserine contains an alpha - amino group ($pK_a = 10$) and, a carboxyl group ($pK_a = 3$) and therefore, the molecule contains two negative charges and one positive charge at pH 7.0, giving it a net negative charge whereby this compound is also within the scope of the invention.

Complex phospholipids having a net positive charge are also within the scope of this invention but are lesser preferred for reasons given above and because of the high price and scarcity of these compounds. Examples of positively charged complex phospholipids within the scope of the invention are those containing the basic acyl amino acid groups. Such compounds are a subgroup within the family of the o-aminoacylphosphatidyl-glycerols.

In contrast to the charged phospholipids, the head groups of phosphatidylethanolamine and phosphatidylcholine (lecithin) have a positive charge at pH 7, and, thus, at this pH, these two phosphoglycerides are dipolar zwitterions with no net electric charge. Such compounds are not within the scope of this invention unless chemically reacted to impart a negative charge to the material.

Of the phospholipids discussed above, the net negatively charged phosphoglycerides are preferred. A more preferred class of phosphoglycerides are represented by the following formula:

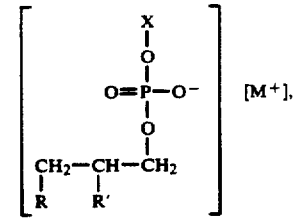

where R and R' are each fatty acid residues preferably having from 8 to 24 carbon atoms; X is hydrogen, a polyol or a 3'-o-aminoacylphosphatidylglycerol; and M is one equivalent of a countercation R and R' are typically common natural fatty acids having an even or odd number of carbon atoms; they may be the same or may differ from each other; and they may be saturated, monounsaturated or polyunsaturated. Examples of fatty acid residues include laurate, myristate, palmitate, stearate, oleate, linoleate, octanoate, dodecate, lignocerate, etc.

Phospholipids are available from a variety of sources such as egg yolks, soy beans, etc. as is known in the art. These sources typically contain a mixture of components including natural lipids as exemplified by glycerides, cholesterol and cholesterol esters; phospholipids having a net charge of zero as exemplified by phosphatidylcholine, phosphatidylethanolamine; various unsaturated and saturated fatty acids; and charged phospholipids such as phosphatidylglycerol and phosphatidylinositol. The charged phospholipids are typically contained in these naturally occurring products in minor concentration, typically varying from below one percent up to 10 to 15 percent of the total composition.

Accordingly, the concentration of the charged phospholipid from such a natural source would likely be insufficient for purposes of treatment in accordance with the invention, and a complex phospholipid having a net charge, preferably a net negative charge, would be added to such a phospholipid source to increase the total concentration of the complex charged phospholipids to a concentration required for treatment in accordance with the invention. Obviously, if a phospholipid from a natural source is negatively charged, a negatively charged phospholipid would be added to supplement the concentration of the same whereby the total net charge remains negative.

The most preferred phospholipid for purposes of this invention is a polyol with a net negative charge. The most preferred polyol phospholipids are the phosphatidylglycerols, including cardiolipins and phosphatidylinositols. Without wishing to be bound by theory, it is believed that the hydroxyl groups of the head groups of these phospholipids participate in hydrogen bonding with the aqueous portion of the tear film thus stabilizing the film formed over the eye for an extended time.

In accordance with the invention, an oil is also applied to the eye as a treatment material. As is known in the art, oils may be derived from animals, plants, nuts, petroleum, etc. Those derived from animals, plant seeds, and nuts are similar to fats and are primarily glycerides or fatty acids and consequently, contain a significant number of acid and/or ester groups rendering the same polar and lesser preferred for purposes of the invention. Alternatively, oils derived from petroleum are usually aliphatic or aromatic hydrocarbons that are essentially free of polar substitution and therefore suitable for purposes of the present invention provided the oil is refined so as to be compatible with human tissue such as the ocular surface. Preferably, the oil is a hydrocarbon oil having from 10 to 50 carbon atoms and more preferably, the oil is a saturated n-alkane or isoalkane hydrocarbon having from 14 to 26 carbon atoms. Unsaturated alkene hydrocarbons may be used but are less chemically stable as the double bonds tend to oxidize. Aromatic oils are lesser preferred because it is known that aromatic compounds are for the most part unsuitable for application to the ocular surface.

The charged phospholipid and non-polar oil may each be topically applied to the surface of the eye separately with the sequence of application preferably comprising first application of the phospholipid and then the oil. Each component may be added to the eye by dispersing each in a carrier liquid such as water to control concentration of the phospholipid or oil and topically applying the dispersed material to the eye. Alternatively, each may be applied to the eye as undiluted materials, though by this method, dosage control is difficult. The oil component is better suited for use in an undiluted form than the phospholipid.

For self-administration, preferably, the oil and the charged phospholipid are applied to the ocular surface as a combined treatment composition dispersed in a liquid carrier such as water. The most preferred treatment composition is a meta-stable oil-in-water emulsion where the oil is the dispersed phase and the aqueous phase is the continuous phase of the emulsion. A meta-stable emulsion can be formed by shaking a mixture of the two materials with water prior to application to the eye. The concentration limits for the treatment composition added to the eye are also suitable for application directly to a prostheses—i.e., a treatment solution in the form of an emulsion.

When the treatment components are dispersed in a carrier, the total volume of treatment composition desirably does not exceed 100 microliters (ul), about 2 standard drops, and more preferably, the total amount varies between about 25 and 50 ul. The amount can be controlled by use of a dispenser that permits addition of a single drop of treatment material to the eye.

If the treatment components are added in undiluted (neat) form, a suitable method of application involves placing a full drop of component on a ball-sphere end of a glass rod dispenser. The drop is desirably shaken leaving a thin surface film of the component on the rod. The tip of the rod is then placed against the inside of the lower lid lining (conjunctiva) and rotated. It is believed that the amount of component dispensed to the eye in this manner is between 1–3 ul.

Other methods of adding the treatment composition such as sprays, injectors, syringes, etc. would be apparent to those skilled in the art.

The total amount of oil added to the eye, whether added as a neat composition, or in the form of an emulsion, preferably does not exceed 25 ul, more preferably varies between about 1 and 10 ul and most preferably varies between about 1 and 5 ul. If the amount of oil added to the eye is in excess of 25 ul, the oil layer on the surface of the eye may be too thick with formation of oil globules on the surface of the eye. This phenomena is likely to result in blurring for a prolonged time. Self-administration of small volumes of oil to the eye is difficult, and for this reason, addition of the oil to the eye in the form of an emulsion is preferred.

In a single treatment composition for both the oil and phospholipid components, the oil component may vary within reasonable limits provided the amount of oil retained on the eye is within the controlled volumes set forth above. A treatment composition containing the oil in a concentration of at least 0.1 percent by weight of the total composition provides some benefits. A preferred concentration for the oil is at least 1.0 percent of the weight of the treatment composition. Preferably, the oil content of the treatment solution varies between about 2.5 and 12.5 percent by weight of the composition.

In the preferred embodiment of the invention where the treatment composition is added to the eye as an emulsion, the total concentration of emulsion added to the eye is desirably controlled to less than 100 ul, and more preferably maintained as low as is practical for self-administration. It should be obvious that if the oil and phospholipid components are added as an emulsion, the concentration by volume of the oil in the emulsion should be controlled to provide the limited dosage of oil described above (10 ul or less) while accounting for that lost by discharge from the eye. For example, if the amount of emulsion added to the eye is 50 ul (a standard drop), the oil content of the emulsion preferably is about 10% by volume, or 5 ul, as a large portion of the oil is likely to be discharged from the eye during the first several blinks following application of the emulsion to the eye.

The concentration of the charged phospholipid in the treatment composition may also vary within wide limits. A treatment composition containing the charged phospholipid in an amount as low as 0.01 weight percent of the total composition provides some benefit. A concentration of charged phospholipid varying between 0.05 to 7.0 percent of the total composition is a clinically practical concentration range for purposes of the invention. It should be noted that the most desired concentration for the charged phospholipid in the composition will vary from subject to subject, though in general, the preferred concentration of the charged phospholipid for a phospholipid deficient subject varies between about 0.05 and 1.0 percent by weight of the total composition, but will vary from patient to patient and other factors known to affect the dry eye condition. Preferably, the ratio of the oil to the phospholipid is at least 100 to 1.

Other additives may be present in the treatment composition including those materials found in phospholipids derived from natural sources such as egg yolk and soy beans. Such materials include minor amounts of neutral lipids and oils such as one or more triglycerides, cholesterol esters, the natural waxes and cholesterol; high molecular weight isoprenoids; stabilizers, surfactants; preservatives; pH adjusters to provide a composition preferably having a pH between about 5.0 and 8.5 and more preferably, between 6.0 and 7.4 and most preferably, between about 6.4 and 7.2; salt, glycerol or sugar in sufficient concentration to form an isotonic or mildly hypotonic composition; etc., all as would be obvious to those skilled in the art.

Of the above additives, certain surfactants are desired to increase the oil concentration that may be contained in a meta-stable emulsion while decreasing the content of the expensive phospholipid component and to increase the rate of spreading of the oil film over the eye. The surfactant selected should be compatible with treatment composition components, compatible with the eye, preferably provide a meta-stable emulsion and not blur vision. Preferred surfactants are polyoxyethylene fatty acid esters and polyoxyethylene alcohol. The surfactant is added to the composition in minor amount, preferably in an amount of less than 1.0 percent by weight and more preferably within a range of from 0.05 to 0.25 percent by weight.

Another useful class of additives are medicaments because the long term stability of the film formed over the surface of the eye using the compositions of the invention results in improved delivery of the medicament to the eye due to increased contact time of the medicament with the eye. Medicaments suitable for delivery to the eye using the film forming compositions of the invention are those soluble in either the aqueous or oil phase of the composition. Illustrative medicaments include antibiotics, antiviral agents, anti-inflammatory agents and antiglaucoma agents such as illustrated in part in published European Patent Application No 0 092 453 published Oct. 26, 1983, sections 5.3.1 and 5.3.2, incorporated herein by reference.

If the treatment composition is in the form of an emulsion, other additives are added to the treatment composition using simple mixing techniques. The concentration of the additive is dependent upon the specific additive, and preferably, total additive content in addition to the charged phospholipid and the oil are at a maximum concentration level whereby the total weight of the organics in the oil phase does not exceed 15 percent of the total weight of the emulsion.

The treatment compositions of the invention are also desirably used with subjects requiring ocular prostheses. In this instance, the treatment composition enhances the tear film layer and lubricates the boundary between the prosthesis and the ocular surface. When used with an ocular prosthesis, the treatment composition may be applied to the inner or both the inner and outer surfaces of the prostheses prior to insertion of the same into the eye. Regardless of how added, the amount available to form the oil layer should be within the limits set forth above.

The invention will be better understood by reference to the examples which follow. In all, a tear film formed over an ocular surface was evaluated by projecting a light source onto the ocular surface and viewing the reflected images from the light source on a video screen. The light source and its location is one that illuminates a surface area on the ocular surface of approximately 10 mm$^2$. Interference patterns are formed, the color(s) of which are indicative of the thickness of the oil layer. The color of the waves are correlated with a protocol of known film thickness. In this way, tear film can be evaluated over a period of real time and rated in accordance with the following scale:

| Rating | Film Characteristics | Quality |
| --- | --- | --- |
| A | Colored waves - particularly greens and blues. Waves extend from lower lid to above the lower pupillary border. Film thickness is excess of 170 nm. | Excellent |
| B | Colored waves - reds, browns, yellows, but no blues. Waves extend from lower lid to above the lower pupillary border, Film thickness of approximately 90 nm to 170 nm. | Good |
| C | Colored waves - only yellow is present. Waves extend from lower lid to lower pupillary border. Film thickness of approximately 90 nm. | Good |
| D | Waves visibile but no color present or no color other than grayish white. Waves extend from lower lid to lower pupillary border. Film thickness of less than 90 nm. | Fair |
| F | No waves and no color. An absence of any observable tear film movement. Film thickness of less than 70 nm. | Poor |

In addition to the above ratings, a numerical format may be utilized to express the change in lipid layer thickness. A numerical grade of 1.0 indicates a change of one letter grade. If a C baseline finding prior to the application of a drop of treatment solution improved the tear film to a B, a numerical grade of 1.0 would be given. A 2.0 numerical grade would indicate a two letter grade improvement and a 3.0 numerical grade would indicate a three letter grade improvement. For many of the following examples, a 3.0 numerical grade represents an improvement from a D to an A, the maximum improvement possible in accordance with the testing method used because subjects with a grade of F were screened and eliminated from testing.

In some examples, the designation (+) or (−) following a letter means a minor deviation from the standard given. In all examples, the eye was evaluated and rated before application of a eye treatment formulation and following application of the formulation.

In the presentation of data in the following examples, different formats are used as the means of collecting data and analyzing the same became better understood as research progressed. For Examples 1 to 3, patient selection was random without screening to provide a control group. For this reason the data is scattered and is not as consistent as the data presented in the remaining examples.

EXAMPLE 1

This example illustrates a dry eye treatment composition in the form of an emulsion made by agitating a phospholipid and oil where applicable in physiologic aqueous vehicle while warming the composition to a temperature in excess of the melting point of the phospholipid component. Agitation is continued at an elevated temperature until a homogeneous dispersion is obtained. Emulsions formed in this manner have relatively large particle size and are of moderate stability. Various test solutions are illustrated as set forth throughout the example. The treatment compositions were applied to the eye from a standard 3 ml droppette bottle. The phosphatidyl choline used was a pure synthesized material. All films were evaluated two minutes following application of the treatment composition to the eye. The first test solution evaluated had the following formulation:

| Formulation 1 | |
|---|---|
| Component | Amount (% by Wt) |
| Phosphatidyl Choline | 0.05 |
| Phosphatidyl Glycerol | 0.05 |
| Sorbic acid | 0.100 |
| Ethylenediaminetetraacetic-acid | 0.100 |
| Glycerol | to osmolarity about 230 |
| Water | to 1 liter |

The results obtained are given in the following table:

| Patient Number | Treatment Formulation | Rating | |
|---|---|---|---|
| | | Before Treatment | After Treatment |
| 1 | 1 | F+ | D |
| 2 | 1 | F | C− |
| 3 | 1 | D | C− |
| 4 | 1 | C | B |
| 5 | 1 | C | C+ |
| 6 | 1 | C | C |
| 7 | 1 | C | C |
| 8 | 1 | C− | C |
| 9 | 1 | B | B |
| 10 | 1 | A | A |
| 11 | 1 | A | A+ |

In essentially all tests, some improvement was obtained, though the improvement varied from subject to subject except for those subjects initially having a good to excellent tear film where the degree of improvement was difficult to observe.

The procedure was repeated using at treatment solution consisting of a phospholipid in combination with a non-polar oil. The test formulation has the following compositions:

| Formulation 2 | |
|---|---|
| Component | Amount (% by Wt) |
| Phosphatidyl Choline | 0.05 |
| Phosphatidyl Glycerol | 0.05 |
| Sorbic acid | 0.100 |
| Ethylenediaminetetraacetic-acid | 0.100 |
| Glycerol | to osmolarity about 230 |
| Alkane Oil[(1)] | 1.000 |
| Water | to 1 liter |

[(1)]Liquid Mineral oil sold under the trade name Drakeol 21 and available from Penreco Corp. of Butler, PA.

The following results were obtained:

| Patient Number | Treatment Formulation | Rating | |
|---|---|---|---|
| | | Before Treatment | After Treatment |
| 12 | 2 | F | D+ |
| 13 | 2 | F | D |
| 14 | 2 | D+ | B |
| 15 | 2 | D | C− |
| 16 | 2 | C | B− |
| 17 | 2 | C | B |
| 18 | 2 | C | C |
| 19 | 2 | C | C+ |
| 20 | 2 | C | A− |
| 21 | 2 | B | B+ |
| 22 | 2 | A | A |
| 23 | 2 | A | A+ |

The procedure was repeated using treatment solutions of a phospholipid in combination with a polar oil. Two different polar oils were evaluated. The formulations of the treatment solutions follow:

| Component | Amount (% by Wt) |
|---|---|
| Formulation 3 | |
| Phosphatidyl Choline | 0.05 |
| Phosphatidyl Glycerol | 0.05 |
| Ethylenediaminetetraacetic acid | 0.100 |
| Sorbic acid | 0.100 |
| Oleic acid palmityl ester | 0.300 |
| Glycerol | to osmolarity about 230 |
| Water | to 1 liter |
| Formulation 4 | |
| Phosphatidyl Choline | 0.085 |
| Phosphatidyl Glycerol | 0.085 |
| Ethylenediaminetetraacetic acid | 0.100 |
| Sorbic acid | 0.100 |
| Myristic acid ethyl ester | 0.300 |
| Glycerol | to osmolarity about 230 |
| Water | to 1 liter |

The following results were obtained;

| Patient Number | Treatment Formulation | Rating | |
|---|---|---|---|
| | | Before Treatment | After Treatment |
| 24 | 3 | F+ | C |
| 25 | 3 | D− | C− |
| 26 | 3 | D | B+ |
| 27 | 3 | C− | B |
| 28 | 3 | C | B− |
| 29 | 3 | C | B+ |
| 30 | 3 | B | B |
| 31 | 3 | B | B− |
| 32 | 3 | B− | B− |
| 33 | 3 | A+ | A |
| 34 | 3 | A− | A− |
| 35 | 3 | A | A |
| 36 | 4 | F | D |
| 37 | 4 | D | C |
| 38 | 4 | D | B− |
| 39 | 4 | C | C+ |

-continued

| Patient Number | Treatment Formulation | Rating Before Treatment | Rating After Treatment |
|---|---|---|---|
| 40 | 4 | C− | B− |
| 41 | 4 | C | B+ |
| 42 | 4 | C | C |
| 43 | 4 | C− | B− |
| 44 | 4 | B+ | B+ |
| 45 | 4 | B | B |
| 46 | 4 | A+ | A |
| 47 | 4 | A− | A− |
| 48 | 4 | A | A |

From the data, it can be seen that treatment with a charged phospholipid without oil improved the tear film in most cases. Combination of the phospholipid with the non-polar oil improved the tear film in practically all cases and though not shown in this example, the retention of the tear film was longer using an oil compared to treatment without oil. Larger concentrations of oil in accordance with the concentration limits taught herein provide even greater improvement. Improvements were also obtained using the polar oil, but blurring was experienced by most patients.

EXAMPLE 2

The treatment compositions herein and their methods of application were the same as those of Example 1, except that the emulsion was formed using procedures of U.S. Pat. No. 4,533,254 thereby producing a very stable emulsion with a finely dispersed oil phase. The emulsion of Example 2 was substantially more stable than the emulsion of Example 1. The compositions examined in the Example are similar to Formulation 1 and 2 of Example 1 except for the method of preparation of the emulsion and a reduction in the concentration of each of the phospholipid components to 0.05 percent. The results obtained are set forth below with Formulation 1' comparable to Formulation 1 of Example 1 and Formulation 2' comparable to Formulation 2.

| Patient Number | Treatment Formulation | Rating Before Treatment | Rating After Treatment |
|---|---|---|---|
| 1 | 1' | F | D |
| 2 | 1' | F | A− |
| 3 | 1' | F | D |
| 4 | 1' | F | C |
| 5 | 1' | F | B |
| 6 | 1' | F | A |
| 7 | 1' | F | F |
| 8 | 1' | F | A+ |
| 9 | 1' | F | B+ |
| 10 | 1' | F | B |
| 11 | 1' | F | D |
| 12 | 1' | D | A |
| 13 | 1' | D+ | B− |
| 14 | 1' | B | A |
| 15 | 1' | B− | B |
| 16 | 1' | B− | A |
| 17 | 1' | A− | A |
| 18 | 2' | F | A |
| 19 | 2' | F | A |
| 20 | 2' | D | A+ |
| 21 | 2' | D | C+ |
| 22 | 2' | C | A |
| 23 | 2' | A | A |

In this example, the use of a charged phospholipid improved results in all but two cases though the results varied significantly from patient to patient. Variation in the results obtained is believed to be due to the presence of some natural oils in the eye with the charged phospholipid assisting in the formation of a controlled oil film over the eye. The results shown in this example were not reproducible with subsequent batches of emulsions formed using the procedures of this Example 2. Though improvements were obtained with all subsequent batches, the results were not as spectacular and blurring occurred with most subjects. Consequently, though microfluidized emulsions were at one time considered to be a preferred embodiment of the invention, a meta-stable emulsion is now considered the preferred embodiment of the invention.

EXAMPLE 3

The following example illustrates addition of oil alone as a tear film additive. Formulations 5 and 6 were neat solutions of safflower oil (a polar oil) and a mineral oil (non-polar oil) respectively. The mineral oil is the same as that used in Example 1, Formulation 2. The emulsion was added by placing a full drop of the treatment solution directly on the eye (about 50 ul). The results obtained one hour after application to the eye are as follows:

| Patient Number | Treatment Formulation | Rating Before Treatment | Rating After Treatment |
|---|---|---|---|
| 1 | 5 | F | F |
| 2 | 5 | D | F |
| 3 | 5 | C | D |
| 4 | 5 | B | C |
| 5 | 5 | A | F− |
| 6 | 5 | A | F |
| 7 | 5 | A | F |
| 8 | 6 | F | A |
| 9 | 6 | F | C |
| 10 | 6 | D | A+ |
| 11 | 6 | F | A+ |
| 12 | 6 | F | A |
| 13 | 6 | B | A+ |
| 14 | 6 | B | A+ |
| 15 | 6 | A | A |
| 16 | 6 | A | A |

The use of a polar oil alone for dry eye treatment resulted in an excessively thick film over the eye with substantial blurring. Use of a non-polar oil in accordance with the invention provided a superior film in most cases but vision was blurred. It is believed that blurring occurred due to the formation of an excessively thick oil film over the ocular surface due to the application of an excessive quantity of oil as a result of the method of administering the oil to the eye. With time, typically in excess of two hours, the film would thin and the film would function for a prolonged residence time without blurred vision.

EXAMPLE 4

The following example demonstrates application of a controlled dosage of a neat (undiluted) non-polar oil to the eye. Three dosages were tested. Dosage 1 was in an amount varying between 1 and 3 ul, dosage 2 in an amount varying between about 5 and 10 ul, and dosage 3 in an amount of about 50 ul. The lowest dosage was administered to the eye by adding a drop of the treatment composition onto the ball-sphere end of a glass rod dispenser. The rod, is then shaken 3 times leaving a thin surface film of the treatment composition on the rod, i.e., approximately 1–3 ul. The tip of the rod is then placed against the inside of the lower lid lining and rotated 360 degrees. Approximately a 2-3 mm area of the rod comes into contact with the conjunctiva dispensing 1-3 ul to the eye. The dosage of from 5-10 ul was administered by measuring a full drop with a microsyringe onto a glass rod constructed with a ball-sphere at one end such that it can only hold a volume of approximately 10 microliters. The ball sphere end of the glass rod is then contacted with the eye. The largest dose was applied by adding a drop of oil to the eye.

Following application of the oil to the eye, the tear film was examined periodically to determine the duration of time the film remained on the eye. For each test, several subjects were examined and the results given are the average of the subjects examined. The results are given in the following table where time is in minutes, dosage is in ul and "Number" refers to the number of subjects tested.

| Formulation I.D. No. | Number of Subjects | One-Time Treatment Dosage in Microliters | Improvement at Time Intervals Following One-Time Treatment Dosage | | | | | Comments |
|---|---|---|---|---|---|---|---|---|
| | | | 2 min. | 30 min. | 60 min. | 120 min. | 240 min. | |
| DR-35 (1) | 11 (2) | 1-3 ul | 2.8 | 2.1 | 1.3 | 0.8 | 0.4 | Film forms quickly and evenly and stays. |
| DR-35 | 11 (2) | 5-10 ul | 2.9 | 2.5 | 1.6 | 1.1 | 1.0 (3) | Film forms quickly and evenly but is thicker than with 1-3 ul. |
| DR-35 | 7 | 50 ul | Excessively thick film & blurred for 1 hr. Tear film then thins & after 1-2 hrs. simulates data above when volume is equivalent to a one-time treatment dosage of 1-10 ul. (Also a residual next day effect = 0.8) | | | | | Film too thick to measure by interference. Results in severe visual blur lasting hours & disabling patient. |
| DR-21 (1) | 7 (2) | 1-3 ul | 3.0 | 2.1 | 1.6 | 1.0 | 0.8 | Fast film formation with insignificant blur. |
| DR-21 | 7 (2) | 5-10 ul | 3.3 | 2.8 | 2.3 | 1.6 | | Fast film formation with insignificant blur. Note 3.3 rating due to "A+" & unusually uniform thick lipid film. |
| DR-15 (1) | 5 | 1-3 ul | 2.9 | 1.6 | 1.5 | 0.7 | 0.3 | Fast film formation with insignificant blur. |
| DR-15 | 6 | 5-10 ul | 2.8 | 2.3 | 1.5 | 1.1 | (0.6) (4) | |
| DR-05 (1) | 5 | 1-3 ul | 2.7 | 1.3 | 1.0 | 0.2 | 0.0 | Spreads well but retention not as good as heavier oils. |
| DR-05 | 3 | 5-10 ul | 2.8 | 2.3 | 1.5 | 1.1 | (0.3) (5) | |
| Pristane (6) | 4 | 1-3 ul | 2.5 | 0.8 | 0.2 | 0.1 | | Film forms quickly & evenly but retention not equal to Drakeol. No blur w/1-10 ul; blur mild with 50 ul. |
| Pristane | 5 | 5-10 ul | 2.4 | 1.5 | 0.8 | 0.2 | | |
| Pristane | 5 | 50 ul | 1.7 | 2.1 | 0.9 | 0.4 | | |

Footnotes
(1) DR refers to Drakeol alkane oil available from Penreco Co. of Butler, PA. The numeral following the letters represents the weight of the oil.
(2) Data combined from different days, and averaged.
(3) Rating of 1.0 at 240 mins. Residual effect next day almost equal at 0.8. Very durable and lasting. With 50 ul drop, residual next day equivalent to that with 5-10 ul drop, or greater.
(4) Residual value of 0.6 applied to next A.M. evaluation.
(5) Residual value of 0.3 applied to next A.M. evaluation.
(6) Pristane oil available from Sigma Chemical Co. of St. Louis, MO.

EXAMPLE 5

The procedure of Example 4 was repeated for purposes of comparison, alkene or polar oils were substituted for the alkane non-polar. The results are set forth below.

| Test Materials | Number of Subjects | One-Time Treatment Dosage in Microliters | Improvement at Time Intervals Following One-Time Treatment Dosage | | | | | Comments |
|---|---|---|---|---|---|---|---|---|
| | | | 2 min. | 30 min. | 60 min. | 120 min. | 240 min. | |
| Squalene | 4 | 1-3 ul | 2.9 | 1.1 | 0.3 | 0.1 | | No blur. Rapid film formation. |
| Squalene | 5 | 5-10 ul | 2.6 | 1.9 | 1.2 | 0.3 | 0.1 | |
| Coconut Oil | 5 | 1-3 ul | 1.5 | 0.8 | 0.7 | 0.4 | 0.1 | Forms globular beaded streaks with some blur. |
| Coconut Oil | 9 (1) | 5-10 ul | 1.9 | 1.2 | 0.8 | 0.7 | | |
| Peanut Oil | 7 | 1-3 ul | 1.5 | 1.4 | 1.0 | 0.3 | | Beaded and irregular with no significant blur. |
| Peanut Oil | 7 | 5-10 ul | 2.0 | 1.7 | 1.3 | 1.0 | | |
| Soybean Oil | 3 | 1-3 ul | 2.0 | 0.8 | 0.2 | 0.2 | | Globular & beaded streaks. Severe visual blur. Not useable. |
| Soybean Oil | 2 | 5-10 ul | 0.0 (2) | 0.7 | 0.2 | 0.0 | | |
| Safflower Oil | 6 | 1-3 ul | 1.4 | 1.7 | 1.0 | 0.3 | 0.2 | 1-3 ul highly erratic, with mild-moderate blur. |
| Safflower Oil | 13 (1) | 5-10 ul | 1.0 (SP) | 1.3 (SP) | 0.8 (SP) | 0.5 (SP) | (2) Above data is for 5-10 ul for 8 subjects. The remaining 5 subjects scored negative values & are not included in the above ratings. The 5-10 ul is at a threshold for severe negative effects and blurring. | SP = Special Phenomenon. Highly variable film. Beady zero rating to dense white sheets of oil slick. 5 of 13 subjects rated minus value. Data for 8 subjects & based on interference colors seen. Vision significantly blurred. |

| Test Materials | Number of Subjects | One-Time Treatment Dosage in Microliters | Improvement at Time Intervals Following One-Time Treatment Dosage | | | | | Comments |
|---|---|---|---|---|---|---|---|---|
| | | | 2 min. | 30 min. | 60 min. | 120 min. | 240 min. | |
| Safflower Oil | 7 | 50 ul | | Tear film severely altered with patches, balls and lumps of oil. Vision severely compromised for avg. of 60 mins., with blur remaining for hours. | | | | Dense & severe negative effects. Severe compromise to vision. |

Footnotes
(1) Data combined from different days, and averaged.
(2) Tear film compromised - no useful thickness increase, although film thicker. Interference phenomenon used for measurement does not record thicknesses over 180-200 nanometers.

The above data shows that polar oils provide improvement but the improvement is less than that provided by the non-polar hydrocarbon or alkane oils.

EXAMPLE 6

This example compares various surfactants used to form an emulsion treatment composition and enable an increase in the amount of oil in the composition. The treatment composition used prepared by homogenization had the following composition:

| Component | Amount (% by Wt) |
|---|---|
| Phosphatidyl Glycerol | 0.10 |
| Ethylenediaminetetraacetic acid | 0.10 |
| glycerol | 2.00 |
| Alkane Oil (1) | 10.00 |
| Surfactant (2) | 0.15 |
| Water | to 1 liter |

(1) The oil used was the liquid hydrocarbon oil identified above as Drakeol 35.
(2) As identified below.

| The surfactants tested are follows: | |
|---|---|
| Formulation 1 | Stearyl ether of polyethoxyethylene sold under the tradename Brij 76 by ICI chemicals |
| Formulation 2 | A polyethylene oxide sold under the tradename Polyox WSR-N750 by Union Carbide |
| Formulation 3 | A polysorbate sold under the tradename Span 60 by ICI in Wilmington, Delaware. |
| Formulation 4 | A polyethoxyethylene stearate sold under the tradename Myrj 52 by ICI chemicals. |
| Formulation 5 | A stearyl ether of a polysorbate sold under the tradename Tween 80 by ICI in Wilmington, Delaware. |

Tear film performance was measured using the same procedures as set forth in Example 1 at various time intervals. In all cases about 25 ul of treatment emulsion were added to the eye. The data obtained is for a composite of many trials. The results obtained are as follows:

| Formulation Number | Improvement at Time Intervals Following One-Time Treatment Dosage | | | |
|---|---|---|---|---|
| | 2 min. | 30 min. | 60 min. | 120 min. |
| 1 | 2.7 | 1.5 | .9 | 0.5 |
| 2 | 1.3 | 0.7 | 0.25 | 0.2 |
| 3 | 2.4 | 1.9 | 1.1 | 0.3 |
| 4 | 2.7 | 1.5 | .9 | .5 |
| 5 | 2.9 | 1.8 | 1.1 | 0.35 |

The above experiments were repeated with the surfactant varying in concentration from 0.02 through 0.3%. The lower concentrations resulted in poor to fair tear film formation up to about 0.05 % surfactant content. Best results were obtained within a range of from 0.05 to 0.15% surfactant. Additional surfactant provided little improvement and blurring occurred at the higher concentrations.

Formulations 1 and 4 represent preferred embodiments of the invention.

We claim:

1. An artificial tear film over the aqueous layer of the eye comprising a complex phospholipid having a net charge over said aqueous layer and a layer of an essentially non-polar oil over said layers, said oil layer being present in an amount sufficient to form a tear film over the ocular surface and in a volume that does not exceed about 25 microliters.

2. The tear film of claim 1 where the the phospholipid has a net negative charge.

3. The tear film of claim 1 where the volume of the non-polar oil ranges between about 1 and 10 microliters.

4. The tear film of claim 3 wherein the volume ranges between about 1 and 5 microliters.

5. The tear film of claim 2 where the phospholipid is present as a consequence of glandular secretion.

6. The tear film of claim 2 where the phospholipid is a phosphatidylglycerol.

7. The tear film of claim 1 having an optical prosthesis thereon.

8. The tear film of claim 7 where the prosthesis is a contact lens.

9. The tear film of claim 1 where the non-polar oil is mineral oil.

10. The tear film of claim 1 where the mineral oil has from 10 to 50 carbon atoms.

11. The film of claim 1 containing a medicament.

12. The film of claim 1 containing a natural wax.

13. A method for reducing evaporation from an aqueous tear film over the surface of an eye, said method comprising applying an essentially non-polar, liquid oil over a film of a charged phospholipid overlying said tear film, said non-polar oil being added in an amount sufficient to form a tear film over the ocular surface an in a volume that does not exceed 25 microliters.

14. The method of claim 13 where the volume of non-polar oil does not exceed 10 microliters.

15. The method of claim 13 where the phospholipid is present as a consequence of glandular secretion.

16. The method of claim 13 where the phospholipid is a negatively charged phospholipid.

17. The method of claim 13 where the non-polar oil is mineral oil.

18. The method of claim 17 where the mineral oil has from 10 to 50 carbon atoms.

19. The method of claim 13 where the treatment composition is applied to the eye in the form of an oil in water emulsion.

20. The method of claim 19 where the emulsion si added to the eye in a volume not exceeding 100 microliters.

21. The method of claim 19 where the emulsion si formed by shaking the components thereof immediately prior to addition to the eye.

22. The method of claim 19 where the emulsion contains a negatively charged phospholipid in a concentration ranging between 0.1 to 7.90 percent by weight of the emulsion and the non-polar oil is present in an amount ranging between 0.2 and 12. 5 percent by weight of the emulsion.

23. The method of claim 19 where the emulsion contains a non toxic, component compatible, surfactant.

24. The method of claim 23 where the surfactant is a member selected from the group of polyoxyethylene fatty acid esters and polyoxyethylene alcohols.

25. The method of claim 19 where the emulsion contains a medicament.

26. The method of claim 19 where the emulsion is applied to the eye by applying the emulsion to an optical prostheses and inserting the prosthesis in the eye.

27. The method of claim 26 where the prosthesis is a contact lens.

28. The method of claim 19 where an optical prosthesis is present in the eye prior to addition of the emulsion.

29. The method of claim 13 where the oil is an undiluted non-polar oil and is added to the eye in a volume ranging between 1 and 10 microliters.

30. The method of claim 29 where the volume ranges between 1 and 5 microliters.

31. The method of claim 29 including a step of insertion of optical prosthesis into the eye following application of the oil to the eye.

32. The method of claim 29 including a step of insertion of optical prosthesis into the eye prior to application of the oil to the eye.

33. The method of claim 13 where the admixture contains a natural wax.

34. The method of claim 13 where the admixture contains a medicant.

35. A treatment composition for topical application to the eye, said composition comprising an aqueous oil in water emulsion of an essentially non-polar oil and a charged phospholipid, said emulsion containing said complex phospholipid and said non-polar oil in an amount sufficient to form a tear film over the ocular surface and in a concentration whereby 1 standard 50 microliter drop of said emulsion will contain from about 1 to 25 microliters of said non-polar oil.

36. The composition of claim 35 containing from about 0.1 to 7.0 percent by weight of the emulsion of a phospholipid having a net negative charge.

37. The composition of claim 35 where the the oil is present in the emulsion in a concentration ranging between 0.2 and 12.5 percent by weight of the emulsion.

38. The composition of claim 36 where the phospholipid component is present in the emulsion in a concentration ranging between 0.1 and 1.0 percent by weight and the oil is present in an amount ranging between 0.5 and 12.5 percent by weight.

39. The composition of claim 35 where the oil is present in the emulsion in a concentration whereby a drop of the emulsion will contain a volume of oil in an amount varying between about 1 and 10 microliters.

40. The composition of claim 39 where the volume ranges between about 1 and 3 microliters.

41. The composition of claim 35 where the emulsion contains a non toxic, component compatible, surfactant.

42. The composition of claim 41 where the surfactant is a member selected from the group of polyoxyethylene fatty acid esters and polyoxyethylene alcohols.

43. The composition of claim 35 where the emulsion contains a medicament.

44. The composition of claim 35 where the oil is mineral oil.

45. The composition of claim 44 where the mineral oil has from 10 to 50 carbon atoms.

46. The composition of claim 35 where the emulsion contains a natural wax.

* * * * *